United States Patent [19]

Tyler, III et al.

[11] 3,933,878

[45] Jan. 20, 1976

[54] LIGAND COMPLEXES OF CU(1)SALTS

[75] Inventors: William E. Tyler, III, Berkeley Heights; Martin B. Dines, Mountainside, both of N.J.

[73] Assignee: Exxon Research and Engineering Company, Linden, N.J.

[22] Filed: Aug. 10, 1973

[21] Appl. No.: 387,445

Related U.S. Application Data

[62] Division of Ser. No. 259,079, June 2, 1972, Pat. No. 3,776,972.

[52] U.S. Cl. ..... 260/438.1; 260/677 A; 260/677 AD
[51] Int. Cl.$^2$ ............................................. C07F 1/08
[58] Field of Search ................................. 260/438.1

[56] References Cited
UNITED STATES PATENTS

| | | | |
|---|---|---|---|
| 2,199,944 | 5/1940 | van Peski et al. | 260/438.1 X |
| 2,362,219 | 11/1944 | Schulze et al. | 260/438.1 X |
| 2,880,223 | 3/1959 | Coates et al. | 260/438.1 |
| 2,900,295 | 8/1959 | Stone | 260/438.1 X |
| 2,909,544 | 10/1959 | Birum | 260/438.1 |
| 2,953,589 | 9/1960 | McCauley | 260/438.1 |
| 3,064,025 | 11/1962 | Warner et al. | 260/438.1 |
| 3,137,692 | 6/1964 | Maier | 260/438.1 X |
| 3,345,392 | 10/1967 | Grayson et al. | 260/438.1 |
| 3,517,080 | 6/1970 | Beckham et al. | 260/438.1 X |
| 3,732,329 | 5/1973 | Thatcher et al. | 260/438.1 X |
| 3,772,268 | 11/1973 | Giles et al. | 260/438.1 X |

FOREIGN PATENTS OR APPLICATIONS 37-11020   8/1962   Japan

OTHER PUBLICATIONS

Dalziel, J. Chem. Soc. (A) p. 357 (1967).

Chuckman et al., Can. J. Chem., Vol. 50, p. 1008 (1972).

Chem. Abstracts, Vol. 63, 5671–5672 (1965).

Chem. Abstracts, Vol. 54, 15244h (1960).

Volponi et al., Inorg. Nucl. Chem. Letters, Vol. 8, pp. 309–312 (1972).

Marsich et al., J. Inorg. Nucl. Chem., Vol. 34, No. 3, p. 936.

Moers et al., J. Inorg. Nucl. Chem., Vol. 32, No. 10, p. 3225 (1970).

Sandhu et al., J. Inorg. Nucl. Chem., Vol. 33, No. 5, p. 1457 (1971).

*Primary Examiner*—Helen M. S. Sneed
*Attorney, Agent, or Firm*—Frank A. Santoro

[57] ABSTRACT

Novel compositions of matter herein are claimed and may be represented by the general formula CuA.L, where CuA is a Cu(I) salt of medium to strong Bronsted acids and L is a ligand chosen from a variety of structural classes including phosphines, phosphites, phosphine sulfides, phosphine oxides, thiophosphates, thioureas or arsines. These compositions are liquid at ambient conditions and are useful for complexing a variety of complexible organic compounds such as olefins, diolefins, allenes, acetylenes, aromatics, carbon monoxide and the like. In a preferred embodiment, the use of trialkyl phosphines is found to improve the stability of $CuAlCl_4$.aromatic systems when said systems are used in olefin complexing processes.

5 Claims, No Drawings

LIGAND COMPLEXES OF CU(1)SALTS

This is a division, of application Ser. No. 259,079 filed June 2, 1972 now Patent No. 3,776,972.

FIELD OF THE INVENTION

This invention relates to a method of preparing novel compositions of matter having the formula CuA.L by contacting the Cu(I) salts of moderate to strong Bronsted acids with suitable ligands in a 1:1 mole ratio. The process may be carried out in the presence of a solvent which is subsequently removed. Alternatively, the materials may be prepared by reacting a Cu(II) salt with an appropriate reducing agent in the presence of a ligand. More particularly, the invention relates to the use of these novel compositions of matter as complexing agent for separating complexible ligands from feed streams.

In a preferred embodiment, the invention relates to the use of a special class of these ligand materials, namely, the trialkyl phosphines for use in a $CuAlCl_4$.aromatic system employed in olefin complexing processes. The addition of said trialkyl phosphines to these systems has been found to improve the stability of the complexing system. The invention, therefore is related to the use of liquid copper salts as complexing agents and in a preferred embodiment as an improvement on the employment of $CuAlCl_4$.aromatic systems, in olefin complexing processes.

DESCRIPTION OF THE PRIOR ART

In general copper (I) salts are known to complex a variety of organic compounds such as olefins and aromatics and the like. This property of the copper salts makes them especially useful as agents to effect various separations. For example, U.S. Pat. No. 3,410,924 describes a process for recovering complexible ligands from feed streams by contacting them with a cuprous halide salt contained in an anhydrous slurry in the presence of a $C_5$ monoolefin sorbent activator.

Another process is described in U.S. Pat. No. 3,218,366 wherein the separation of olefins from hydrocarbon mixtures is carried out via a selective absorption method with a silver fluoroborate or a silver fluorosilicate. The separation of nonaromatic unsaturated hydrocarbons from more saturated hydrocarbons by selective complex formation with cuprous trifluoroacetate dissolved in solvents, such as propionitrile or the like has been disclosed in U.S. Pat. No. 3,401,112.

Beckham et al in U.S. Pat. No. 3,517,081 teaches a process for the separation of unsaturated hydrocarbons in admixture with saturated hydrocarbons by contacting the feed with cuprous fluoroborate or cuprous fluorophosphate dissolved in aromatic hydrocarbon solvents such as toluene, ethylbenzene, ethyltoluene, xylenes and the like.

In Ser. No. 805,912 now U.S. Pat. No. 3,651,159 and U.S. Pat. No. 3,592,865 there is described the preparation and use of bimetallic salts, i.e., cuprous tetrachloroaluminate ($CuAlCl_4$) dissolved in aromatic hydrocarbons, i.e., benzene, as being useful for the separation and recovery of complexible ligands by a ligand exchange process.

Mono-triaryl phosphine complexes of copper (I) salts are known, [See for example, *Journal of Inorganic Nuclear Chemistry*, G. Costa et al, 27, 2581 (1965)], however, these complexes exist as insoluble, solid tetramers and are not, within the scope of the present invention, said invention describing novel ligand Cu(I) complexes which are liquids, under ambient conditions.

The usefulness of the copper salts as complexing agents are enhanced if they are in a liquid state. Accordingly, it has been found that liquid copper salts, which may be prepared by the present invention, are useful as complexing agents and therefore represent an advance in this art.

SUMMARY OF THE INVENTION

In accordance with the present invention, novel ligand complexes of Cu(I) salts having the general formula CuA.L are described. More particularly, a method of separating complexible ligands contained in a feed stream by complexing with said complexes, is also described.

This method comprises contacting the feed stream with the ligand cuprous complexes in the liquid state having the above formula whereby a portion of the complexible ligands are removed from the feed stream. In a preferred embodiment, an improved olefin complexing process is described comprising the steps of contacting the feed stream containing the olefin with a sorbent material containing $CuAlCl_4$ in low volatility aromatic solvents and complexing a substantial portion of the olefins, thereby removing them from the feed stream, followed by decomplexing to recover the olefin, the improvement comprises incorporating a sufficient amount of trialkyl phosphine into the complexing solution.

It has been unexpectedly discovered that the addition or incorporation of this special class of ligands, i.e., trialkyl phosphines into the complexing solution provides increased stability for the cuprous tetrachloroaluminate system when operated in the presence of olefins by providing the following: (1) it lowers the melting point of the olefin complex; (2) makes the system homogeneous; and (3) it stabilizes the system by helping to maintain copper as Cu(I) while reducing alkylation and polymerization side reactions.

The preparation of the novel ligand complexes of Cu(I) salts is carried out by the direct mixing of suitable amounts of ligand with a Cu(I) salt. By Cu(I) salt is meant, a cuprous salt of medium to strong Bronsted acids. Bronsted acids may be defined in terms of their $H_o$ valve [Hammet acidity function defined in *Journal of the American Chemical Society* 54, 273, 2731 (1932)], that is medium to strong Bronsted acids will generally have $H_o$ values in the range of from 5 to −20, more preferably from 0 to −18, and most preferably from −10 to −18.

The ligand employed in the preparation of the liquid copper complexes may be chosen from a variety of structural classes, which will form a 1:1 liquid adduct with the Cu(I) salt. Included within the various classes of useful ligand materials are moieties such as; phosphines, phosphites, phosphine sulfides, thiophosphates, thioureas and arsines. These compounds may comprise alkyl, alkylaryl or aralkyl groups and any combination of such groups. For example, ligands having the formula $R_1R_2R_3P$ which are referred to as phosphine ligands, wherein $R_1$, $R_2$ and $R_3$ are alkyl radicals having from 1 to 30 carbon atoms, more preferably from 3 to 12 and most preferably from 4 to 8 carbon atoms. Particularly preferred is the tri-n-butyl and tri-n-octyl phosphines. Nonlimiting examples of representative materials which could be used as ligands to prepare the liquid copper salts include: tributyl phosphine, trioctyl phosphine, trihexadecyl phosphine, decyl dimethyl phosphine, trihexyl phosphite, tributyl phosphine sulfide, tripentyl thiophosphate, tributyl arsine, tetraethyl thiourea and the like.

As was previously described, the Cu(I) salts employed in the preparation of the novel liquid copper complexes are those Cu(I) salts of medium to strong Bronsted acids. The compositions of matter prepared have the general formula CuA.L, wherein A is an anionic moiety selected from the group consisting of chloride, cyanide, fluoroborate, trifluoromethane-sulfonate, tetrachloroaluminate, trifluoroacetate, thiocyanate ions and moieties having formulas $PF^-_6$, $AsF^-_6$, $SbF^-_6$, $TeF^-_6$ and $NbF^-_6$. Preferably, however, A is $AlCl^-_4$ and L is a trialkyl phosphine.

The liquid copper complexes, as described above, may be prepared by the direct mixing of appropriate amounts of ligand in Cu(I) salt. They may also be prepared by contacting a Cu(II) salt with an appropriate reducing agent such as alkyl aryl phosphines in the presence of a suitable ligand material. Representative examples of the liquid copper complexes which may be prepared in the aforesaid manner are as follows: $Bu_3P\cdot CuCl$, $Bu_3P\cdot CuO_2CCF_3$, $Bu_3P\cdot CuO_3SCF_3$, $(Bu_3P)_{1.3-5}CuSbF_6$, $Bu_3P\cdot CuCn\cdot \phi\text{-}CH_3$, $(Bu_3P)_2CuBr$, $Bu_3P\cdot CuBF_4$, $Bu_3P\cdot CuNO_3$, $Bu_3P\cdot CuPF_6$, $Bu_3P\cdot CuAsF_6$, $Bu_3P\cdot CuTaF_6$, $Bu_3P\cdot CuNbF_6$.

The liquid copper complexes prepared in the manner described above are useful in a method for separating ligands from feed streams containing them. These complexes may be used to complex and separate a variety of organic compounds such as olefins, diolefins, allenes, acetylenes and aromatics both substituted and unsubstituted. By substituted organic compounds is meant those moieties described above which are substituted with one or more functional groups such as halogen, ester, carbonyl, ether groups and the like attached to the organic compounds.

In a typical reaction sequence, a mixture of gaseous olefin and alkane is bubbled through the liquid copper complex. After saturation, the complex is removed from the gas stream and the desired olefin may then be recovered by heating or by displacement reactions.

In another preferred embodiment, it has been unexpectedly discovered that the inclusion of a sufficient amount, i.e., from 10 mole % up to 200 mole % based on moles of copper, of a trialkyl phosphine having the formula $R_1R_2R_3P$ may be incorporated into a complexing solution containing cuprous tetrachloroaluminate i.e., $CuAlCl_4$, in various low volatile aromatic solvents. The complexing solution is then found to have increased stability in an improved olefin complexing process.

DESCRIPTION OF THE PREFERRED EMBODIMENTS

In a preferred embodiment of the invention described herein, liquid copper complexes are prepared by the reaction of Cu(I) salts of moderate to strong Bronsted acids with trialkyl phosphines, particularly tri-n-butyl and tri-n-octyl phosphines. The complexes are prepared by contacting the two reactants either in the presence of a solvent, which is subsequently removed, or in the absence of a solvent.

A typical process scheme for the use of the liquid copper complexes for separating the various complexible ligands may be described as a process in which a mixture of gaseous olefins and alkanes is bubbled through the liquid copper complex. After saturation of the complex, the complex would be removed from the gas stream and the desired olefin could thereafter be recovered by heating or displacement techniques.

In a preferred embodiment of the improved olefin complexing process, ethylene and propylene may be recovered from the feed stream, the feed stream may be obtained from the light ends section of a conventional steam cracking unit. The desired ligands can be recovered in purities exceeding 95% by the process of this invention wherein the improvement comprises incorporating into the tetrachloroaluminate complexing solution, dissolved in low volatile aromatic solvents, from 10 mole % to 200 mole % of trialkyl phosphines, such as tri-n-butyl phosphine. The process may then be carried out such that the olefins are recovered in the desired purity while at the same time the complexing system is maintained in a homogeneous state and stabilized to reduce alkylation and polymerization side reactions.

The present invention may be illustrated but is not necessarily limited to the following examples:

EXAMPLE I

Tributyl phosphine (20.2 g.–0.10 moles) was added to cuprous chloride (12.0 g.-0.12 moles) in a flask protected by a nitrogen bubbler and stirred overnight. The reaction was filtered in a dry box to give a clear liquid. Analysis: calculated for $C_{12}H_{27}CuClP$: Cu, 21.1; P, 10.3. Found: Cu, 22.9; P, 9.3. This material was found to complex weakly with ethylene, cyclohexene, and 1,5-cyclooctadiene. It was also observed to complex with 1,3-butadiene.

EXAMPLE II

To a benzene solution of 0.01 m. $CuBF_4$ was added 2.02 g. (0.01 m) tributyl phosphine. The solution (light yellow after 1 hour) was stripped of solvent. The remaining oil was used to complex ethylene. It was found that one mole of ethylene was quickly absorbed per mole of copper at room temperature (25°C). and that warming to 40°–70° effected decomplexation quantitatively. The cycle was repeated four times with no loss of activity.

In a similar manner the following Cu(I) salts were prepared as 1:1 liquid adducts with tri-n-butylphosphine: CuCN, $CuOSO_2CF_3$, $CuAlCl_4$, $CuOCOCF_3$ and CuSCN. Analysis indicated the structural formulas corresponded to 1:1 adducts of the ligand tri-n-butylphosphine and the particular salt described above.

The observation of miscibility in all proportions of these complexes with alkanes is good evidence that they are not merely solutions of copper (I) salts in trialkyl phosphine, but rather 1:1 complexes of ligand and the Cu(I) salt and that a substantial bond, i.e., coordinating covalent bond, between phosphorus and copper exists. Otherwise the copper salt would be expected to precipitate upon dilution with alkanes as their solubility in alkanes is very limited and most of the copper salts, described herein demonstrate no solubility at all in alkanes as solvents.

EXAMPLE III

One gram of each of the below listed tributyl phosphine Cu salt complexes was contacted with 1,3-butadiene at one atmosphere pressure and 22°C. In all cases the tri-n-butyl phosphine-Cu salt complex was a liquid at the operating temperature and had the composition indicated by the formulas listed. The results of these experiments are summarized in the table below and show the complexing ability of each of the compounds exemplified, for 1,3-butadiene.

TABLE I

| COMPOUND | MOLES 1,3-BUTADIENE/MOLES Cu |
|---|---|
| $Bu_3P.CuCl$ | .11 |
| $Bu_3P.CuO_2CCF_3$ | .82 |
| $Bu_3P.CuO_3SCF_3$ | .88 |
| $(Bu_3P)_{1.35}CuSbF_6$ | 3.67 |
| $Bu_3P.CuCN.\phi\text{-}CH_3$ | .51 |
| $(Bu_3P)_2 CuBr$ | .46 |
| $Bu_3P.CuBF_4$ | 1.16 |
| $Bu_3P.CuNO_3$ | .40 |

EXAMPLE IV

Tri-n-butyl phosphine-cuprous chloride ($6.0_g$–0.02 moles), biphenyl ($3.0_g$–0.02 moles) and aluminum chloride ($2.6_g$–0.02 moles) were mixed together under a dry nitrogen atmosphere, then heated to 150°C for 12 hours. This was centrifuged to give a clear amber liquid. At 25°C and one atmosphere of ethylene, the complex absorbed 55cc. of ethylene (one molar equivalent equals 56cc.) and at 75°C evolved 53cc. When the temperature was again lowered to 25°, it reabsorbed 53cc. The liquid was taken to various temperatures and the rate of olefin uptake measured. The data is presented in the table below and shows the effect that temperature may have on the complexing rate of a tri-n-butylphosphine- $CuAlCl_4$ in biphenyl complexing solution.

| Temperature (°C) | Rate(moles olefin/mole Cu/hr) | Time Interval(Hr.) |
|---|---|---|
| 100° | .0033 | 22.25 |
| 140° | .0088 | 22.25 |
| 160° | .0042 | 23.25 |

EXAMPLE V

To a solution of trioctyl phosphine (14.86g), in 25 ml. of pentane, was added cuprous chloride (4.16g). The mixture was heated to 100°C for 2 hours with agitation, then allowed to cool and sit overnight. The pentane was stripped off to give a clear colorless liquid. This liquid was analyzed and the analysis showed: Analysis: calculated for $CuClC_{24}H_{51}$ P: Cu, 13.53; P, 6.59. Found: Cu, 13.57; P, 6.61.

EXAMPLE VI

To a solution of tri-n-butyl arsine in pentane is added an equi-molar amount of cuprous chloride. The reaction is stirred for 24 hours until a clear solution is obtained. The solvent pentane, is stripped off to yield a colorless, clear liquid having the following structural formula: $CuCl.(C_4H_9)_3As$.

What is claimed is:

1. Novel compositions of matter having the general formula $CuAlCl_4.L$ wherein L is selected from the group consisting of tributyl phosphine, trioctyl phosphine, trihexadecyl phosphine, decyl dimethyl phosphine.

2. Compositions of matter having the general formula $CuAlCl_4.L$ wherein L is a phosphine having the formula $R_1R_2R_3P$, wherein $R_1$, $R_2$ and $R_3$ are independently selected from the group consisting of alkyl radicals having from 1–30 carbon atoms and which form 1:1 liquid adducts with $CuAlCl_4$ moiety under ambient conditions.

3. The compositions of matter of claim 2 wherein $R_1$, $R_2$ and $R_3$ are independently selected from the group consisting of alkyl radicals having from 3 to 12 carbon atoms.

4. The compositions of matter of claim 2 wherein $R_1$, $R_2$ and $R_3$ are independently selected from the group consisting of alkyl radicals having from 4 to 8 carbon atoms.

5. The compositions of matter described by claim 2 wherein L is further selected from the group consisting of trin-butyl phosphine and tri-n-octyl phosphine.

* * * * *